United States Patent
Biatry

(12) 
(10) Patent No.: US 6,506,391 B1
(45) Date of Patent: Jan. 14, 2003

(54) COSMETIC OR DERMATOLOGICAL COMPOSITION IN THE FORM OF A DISPERSION OF AN OILY PHASE AND AN AQUEOUS PHASE, STABILIZED WITH CUBIC GEL PARTICLES

(75) Inventor: Bruno Biatry, Vincennes (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/347,101

(22) Filed: Jul. 2, 1999

(30) Foreign Application Priority Data

Jul. 3, 1998 (FR) .............................. 98 08559

(51) Int. Cl.$^7$ .............................. A61K 7/00; A61K 7/28; A01N 37/00
(52) U.S. Cl. ...................... 424/401; 424/401; 424/400; 424/70.21; 514/557; 514/558; 514/937; 514/938; 514/941; 514/943
(58) Field of Search .............................. 424/401, 70.21, 424/400; 514/937, 938, 943, 941, 557–558

(56) References Cited

U.S. PATENT DOCUMENTS

| | | | | |
|---|---|---|---|---|
| 5,444,041 A | * | 8/1995 | Owen et al. .................... | 514/2 |
| 5,756,108 A | | 5/1998 | Ribier et al. | |
| 5,759,526 A | * | 6/1998 | Simonnet et al. .............. | 424/59 |
| 6,071,524 A | * | 6/2000 | Riber et al. .................. | 424/401 |

FOREIGN PATENT DOCUMENTS

EP    0 711 540    5/1996
WO    WO 95/34287    12/1995

OTHER PUBLICATIONS

John Seddon; "An Inverse Face–Centered Cubic Phase Formed by Diacylglycerol–Phosphatidylcholine Mixtures"; Biochemistry, vol. 29, No. 34, pp. 7997–8002; 1990; XP000612108.

Marc S. Leaver; "Phase Behaivour and Structure in a Non–ionic Surfactant–Oil–Water Mixture"; J. Chem. Soc., Faraday Trans.; vol. 91, No. 23, pp. 4269–4274; XP 002100883.

Kare Larsson; "The Structure of Mesomporphic Phases and Micelles in Aqueous Glyceride Systems"; Zeitschrift Für Physikalische Chemie Neue Folge; vol. 56, No. 3–4, pp. 173–198; XP 002100884.

U.S. patent application Ser. No. 08/989,853, filed Dec. 12, 1997, pending.

U.S. patent application Ser. No. 09/347,101, filed Jul. 2, 1999, pending.

* cited by examiner

*Primary Examiner*—Russell Travers
*Assistant Examiner*—S Sharareh
(74) *Attorney, Agent, or Firm*—Oblon, Spivak, McClelland, Maier & Neustadt, P.C.

(57) ABSTRACT

W/O or O/W stable dispersions are formed by mixing an oily phase and an aqueous phase when the dispersion is stabilized with cubic gel particles formed by the combination of two amphiphilic compounds, one of the amphiphilic compounds being capable of forming a lamellar phase in the presence of water, and the other being capable of forming an inverse hexagonal phase in the presence of water.

16 Claims, No Drawings

COSMETIC OR DERMATOLOGICAL COMPOSITION IN THE FORM OF A DISPERSION OF AN OILY PHASE AND AN AQUEOUS PHASE, STABILIZED WITH CUBIC GEL PARTICLES

BACKGROUND OF THE INVENTION

1. Field of the Invention

The present invention relates to a composition in the form of a dispersion of an oily phase and an aqueous phase, the dispersion being stabilized with cubic gel particles formed using a combination of two amphiphilic compounds, as well as to the use of the said composition, in particular in the cosmetic, dermatological and/or pharmaceutical fields, more particularly for the care and/or conditioning and/or hygiene and/or making up of the skin, mucous membranes, the scalp and/or the hair.

2. Discussion of the Background

A large variety of products have the form of a dispersion of an oily phase and of an aqueous phase. It is possible for the internal phase to be aqueous (water-in-oil or W/O emulsion) or oily (oil-in-water or O/W emulsion). This relates most particularly to cosmetic, dermatological or pharmaceutical topical products, in which dispersions give the skin good sensory properties. However, it is well known that these dispersions lack stability over time and "break", giving rise to two separate phases which makes them unusable. In order to stabilize these dispersions, an emulsifier is usually added thereto; the nature and concentration of the emulsifier used can significantly influence the stability of such compositions. In addition, it is quite certain that the choice and concentration of a suitable emulsifier will depend on various factors, and in particular on the oil(s) constituting the oily phase of the dispersion or emulsion. Moreover, certain emulsifiers are not without drawbacks, in particular when they are used in high concentration in order to improve the stability of the dispersion. They can cause irritation, in particular on sensitive skin.

To overcome this drawback, document EP-A-711,540 has proposed stabilizing O/W dispersions with cubic gel particles. The term "cubic gel" denotes transparent gels, in the form of a cubic liquid crystal phase. which are isotropic in polarized light. The cubic phases are organized in a bipolar manner in separate hydrophilic and lipophilic domains, in close contact and forming a thermodynamically stable three-dimensional lattice. Such an organization has been described in particular in "La Recherche", Vol. 23, pp 306–315, March 1992, and in "Lipid Technology", Vol. 2, No. 2, pp. 42–45, April 1990. Depending on the arrangement of the hydrophilic and lipophilic domains, the cubic phase is said to be of normal or inverse type. The term "cubic gel" as used according to the present invention includes, of course, gels with different types of cubic phases. However, the technique described in document EP-A-711,540 has the drawback of allowing only O/W emulsions to be obtained.

Surprisingly, it has now beer found that both W/O and O/W stable dispersions or emulsions can be obtained using cubic gel particles, obtained from a mixture of two amphiphilic compounds which are capable of reacting in a different manner in the presence of water. For example, one of the amphiphilic compounds is capable of forming a lamellar phase and the other is capable of forming an inverse hexagonal phase.

SUMMARY OF THE INVENTION

A subject of the present invention is a composition in the form of a dispersion comprising an aqueous phase and an oily phase, characterized in that it also comprises cubic gel particles, formed by mixing together at least two amphiphilic compounds, one of the amphiphilic compounds being capable of forming a lamellar phase in the presence of water, and the other being capable of forming an inverse hexagonal phase in the presence of water.

The mixture of the two amphiphilic compounds forming the cubic gel particles is characterized in that neither of the two amphiphilic compounds can by itself lead to a cubic phase when it is placed in contact with water and that only their mixture leads to such a phase, and that, moreover, one of the amphiphilic compounds is capable of forming a lamellar phase in the presence of water, while the other amphiphilic compound is capable of forming an inverse hexagonal phase in the presence of water.

DETAILED DESCRIPTION OF THE INVENTION

The term "lamellar phase" (phase D according to Ekwall) means a liquid crystal phase with plane symmetry, comprising several amphiphilic bilayers arranged in parallel and separated by a liquid medium which is generally water.

The term "inverse hexagonal phase" (phase F according to Ekwall) means a liquid crystal phase corresponding to a hexagonal arrangement of parallel cylinders filled with a liquid medium which is generally water, separated by a hydrocarbon-based environment corresponding to the fatty chains of the amphiphile. A more precise description of these phases can be found in Revue Francaise des Corps Gras, No. 2, February 1969, pp. 87 to 111 (Lachampt et Vila, "Textures des phases paracristallines" [Textures of paracrystalline phases]), incorporated herein by reference.

The amphiphilic compound capable of forming a lamellar phase is preferably chosen from diglycerol monoesters, such as diglyceryl isostearate (Solvay) and diglyceryl monooleate (Rylo PG 29® sold by Danisco), alone or as a mixture.

The amphiphillic compound capable of forming an inverse hexagonal phase is preferably chosen from diglycerol mono-, di- or triesters, aminopolyol carbamates and mixtures thereof. Examples of diglycerol mon-, di- or triesters are diglyceryl 2-decyltetradecanoate and diglyceryl di-/trioleat (TSED 396® sold by Danisco). Examples of aminopolyol carbamates are 3-N-(2-decyltetradecyloxycarboxyl)amino-1,2-propanediol and N-2-dodecyldexadecyloxycarbonyl-N-methyl-D-glucamine. These aminopolyol carbamates are described in document U.S. Pat. No. 5,788,992, incorporated herein by reference.

The mixture of the two types of amphiphilic compound can contain 10, 20, 30, 40, 50, 60, 70, 80, or 90% of at least one amphiphilic compound capable of forming a lamellar phase, inclusive of all values and subranges therebetween. Preferably, the mixture consists of from 10 to 90% by weight and more preferably 15 to 85% by weight of at least one amphiphilic compound capable of forming a lamellar phase. The mixture can also contain 10, 20, 30, 40, 50, 60, 70, 80, or 90% of at least one amphiphilic compound capable of forming an inverse hexagonal phase, inclusive of all values and subranges therebetween. Preferably, the mixture contains from 10 to 90% by weight and more preferably from 15 to 85% by weight of at least one amphiphilic compound capable of forming an inverse hexagonal phase, relative to the total weight of the mixture.

The ratio between the two types of amphiphilic compound depends on the compounds used, and a person skilled in the art will know how to determine the amount of each type of compound to be used in order to obtain cubic gel particles. For example, the mixtures constituting the cubic gel particles of the compositions of the invention are preferably prepared using the following combinations:

55 to 75% by weight of diglyceryl isostearate and 25 to 45% by weight of diglyceryl 2-decyltetradecanoate;

30 to 65% by weight of diglyceryl isostearate and 35 to 70% by weight of diglyceryl di-/trioleate;

75 to 85% by weight of diglyceryl isostearate and 15 to 25% by weight of 3-N-(2-decyltetradecyloxycarbonyl) amino-1,2-propanediol;

55 to 75% by weight of diglyceryl isostearate and 25 to 45% by weight of N-2-dodecylhexadecyloxycarbonyl-N-methyl-D-glucamine;

15 to 50% by weight of diglyceryl monooleate and 50 to 85% by weight of diglyceryl di-/trioleate.

The composition can comprise 0.1, 1, 2, 3, 4, 5, 6, 7, 8, 9, 10, 11, 12, 13, 14, or 15% of amphiphilic compounds constituting the particles of the cubic phase, inclusive of all values and subranges therebetween. The composition preferably comprises from 0.1 to 15% by weight and better still from 0.5 to 10% by weight of amphiphilic compounds constituting the particles of the cubic phase, relative to the total weight of the composition, and/or from 2 to 40% by weight of oily phase relative to the total weight of the composition.

The weight ratio of the amphiphilic compounds constituting the particles of the cubic phase and of the oily phase preferably ranges from 0.02/1 to 1/1 and better still from 0.05/1 to 0.5/1. The weight ratio of the amphiphilic compounds constituting the particles of the cubic phase and of the oily phase can also be 0.03/1, 0.04/1, 0.05/1, 0.06/1, 0.07/1, 0.08/1, 0.09/1, 0.1/1, 0.2/1, 0.3/1, 0.4/1, 0.5/1, 0.6/1, 0.7/1, 0.8/1, 0.9/1, or 1/1, inclusive of all values and subranges therebetween.

In the composition according to the invention, the cubic gel particles have a size of 0.05, 0.1, 0.2, 0.3, 0.4, 0.5, 0.6, 0.7, 0.8, 0.9, or 1 μm, inclusive of all values and subranges therebetween, preferably ranging from 0.05 μm to 1 μm.

When the composition is an O/W emulsion, the size of the droplets in the oily phase dispersed in the aqueous phase with the aid of these particles is 0.1, 0.2, 0.3, 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, or 10 μm, inclusive of all values and subranges therebetween, preferably ranging from 0.1 to 10 μm.

The composition according to the invention can also contain a dispersing and stabilizing agent chosen from surfactants which are water-soluble at room temperature, containing a saturated or unsaturated, linear or branched fatty chain containing from 8 to 22 carbon atoms. This agent is present in an amount of 0.1, 0.2, 0.3, 0.4, 0.5, 0.6, 0.7, 0.8, 0.9, 1, 1.5, 2, 2.5, or 3% of the total weight of the composition, inclusive of all values and subranges therebetween, preferably in an amount ranging from 0.1 to 3% of the total weight of the composition.

The dispersing and stabilizing agent as defined above is preferably chosen from:
(1) alkyl or alkenyl ethers or esters of a polyol;
(2) N-acyl amino acids and derivatives thereof, as well as peptides N-acylated with an alkyl or alkenyl radical, and the salts thereof;
(3) alkyl or alkenyl ether or ester sulphates, derivatives thereof and salts thereof;
(4) polyoxyethylenated fatty alkyl or alkenyl ethers or esters;
(5) polyoxyethylenated alkyl- or alkenylcarboxylic acids and salts thereof;
(6) N-alkyl or alkenyl betaines;
(7) alkyl- or alkenyltrimethylammonium and salts thereof, and
(8) mixtures thereof.

In the compounds listed above, the alkyl and alkenyl groups preferably contain from 8 to 22 carbon atoms and mixtures of different alkyl and/or alkenyl groups may be present in the dispersing and stabilizing agent.

The alkyl or alkenyl ethers or esters of a polyol may be, for example, polyoxyethylenated alkyl or alkenyl esters of sorbitan comprising at least 20 ethylene oxide units, such as sorbitan palmitate 20 EO or Polysorbate 40 sold under the name Montanox 40 DF® by SEPPIC, and sorbitan laurate 20 EO or Polysorbate 20 sold under the name Tween 20® by ICI. In addition, the alkyl or alkenyl ethers or esters of a polyol may also be, for example, alkyl or alkenyl esters of polyglycerol comprising at least 10 units derived from glycerol, which may or may not be oxyethylenated, such as polyglyceryl-10 laurate sold under the name Decaglyn 1-L® by Nikko Chemicals, and alkyl or alkenyl ethers or esters of mono- or polysaccharides, such as those derived from glucose, fructose, galactose, maltose or lactose, in particular the monoesters at 1- and 6- of D-fructose, of decylglucose and of decylpolyglucose.

The 2- N-acyl amino acids and derivatives thereof, peptides N-acylated with an alkyl or alkenyl radical and salts thereof may be, for example, those for which each alkyl or alkenyl group contains at least 12 carbon atoms. According to the invention, the term "amino acids" refers to α, β, γ-amino acids. N-acyl amino acid salts may be, for example, those of N-acyl glutamate, such as monosodium cocoylglutamate, monosodium lauroylglutamate, disodium ($C_{14}$–$C_{20}$)alkylglutamate (the $C_{14}$–$C_{20}$ alkyl radical being derived from hydrogenated tallow), sold, respectively, under the names Acylglutamate CS-11®, Acylglutamate LS-11® and Acylglutamate HS-21® by Ajinomoto, as well as N-acyl lysines such as lauroyllysine sold under the name Amihope LL® by Ajinomoto. The N-acyl amino acid derivatives, and the salts thereof, are preferably N-acyl sarcosinates such as sodium lauroylsarcosinate sold under the name Oramix L30® by SEPPIC, sodium myristoylsarcosinate and sodium palmitoylsarcosinate sold, respectively, under the names Nikkol Sarcosinate MN® and Nikkol Sarcosinate PN® by Nikko Chemicals. N-acyl peptides may be, for example those derived from all or part of collagen or of keratin, such as sodium lauroyl collagen and palmitoyl keratin sold, respectively, under the names Proteol B 30® and Lipacide PK® by SEPPIC.

The 3-alkyl or alkenyl ether or ester sulphates, derivatives thereof, and salts thereof, may be, for example, those for which the alkyl or alkenyl groups each preferably contain at least 12 carbon atoms. Among the alkyl or alkenyl ether sulphates which are preferably used are alkyl ether sulphate salts and, in particular, sodium lauryl ether sulphate. The alkyl or alkenyl ester sulphates may be, for example, isothionic acid esters and salts thereof, and in particular sodium cocoylisothionate sold under the name Geropon AC 78® by Rhône-Poulenc.

The 4-polyoxyethylenated fatty alkyl or alkenyl ethers or esters are preferably, for example, those for which the alkyl or alkenyl group each contain at least 12 carbon atoms. Those which contain at least 20 ethylene oxide units, such as, for example, PEG-20 stearate, Laureth-23, Oleth-20 and PEG-25 phytosterol, are particularly preferred.

The 5-polyoxyethylenated alkyl- or alkenylcarboxylic acids, and salts thereof, are preferably those containing at least 10 ethylene oxide units, such as, for example, Laureth-10 carboxylic acid and Oleth-10 carboxylic acid.

The 6- N-alkyl or alkenyl betaines are preferably those for which each of the alkyl or alkenyl groups contain at least 12 carbon atoms, such as, for example, laurylamidopropylbetaine and oleylamidopropylbetaine.

The 7-alkyl- or alkenyltrimethylammonium salts are preferably those for which the each of the alkyl or alkenyl groups contain at least 12 carbon atoms. Such salts are preferably bromides and chlorides, such as cocoyltrimethylammonium chloride and cetyltrimethylammonium bromide.

According to one specific embodiment of the invention, the composition according to the invention also comprises from 0.0005% to 5% by weight and preferably from 0.001% to 2% by weight of at least one water-insoluble ionic amphiphilic lipid, relative to the total weight of the composition.

The following are examples of water-insoluble ionic amphiphilic lipids:

(i) phospholipids such as natural phospholipids, for example, soya lecithin or egg lecithin, chemically or enzymatically modified phospholipids such as hydrogenated lecithin or the sodium salt of phosphatidic acid, and synthetic phospholipids such as dipalmitoylphosphatidylcholine;

(ii) phosphoric esters of a fatty alcohol, such as monocetyl phosphate and its sodium and potassium salts, sold under the name Monafax 160® by Mona, as well as dimyristyl phosphate and its sodium and potassium salts, sold under the name Mexoryl SY® by Chimex;

(iii) N-acyl derivatives of glutamic acid, such as the monosodium stearoyl glutamate sold under the name Acylglutamate HS 11® by Ajinomoto and the monosodium cOCOyl-($C_{14}$–$C_{20}$)alkylglutamate mixture, the $C_{14}$–$C_{20}$ alkyl radical being derived from hydrogenated tallow, sold under the name Acylglutamate GS 11® by Ajinomoto;

(iv) sodium cetyl sulphate sold under the name Nikkol SCS® by Nikko Chemicals;

(v) sodium cocoyl monoglyceride sulphate sold under the name Nikkol SGC 80 N® by Nikko Chemicals; and (vi) quaternary ammonium derivatives, such as behenyltrimethylammonium chloride, dilauryldimethylammonium chloride, distearydimethylammonium chloride, 4,5-dihydro-1-methyl-2-($C_{14}$–$C_{20}$)alkyl-1-(2-($C_{14}$–$C_{20}$)alkylaminoethyl)imidazolium methyl sulphate, in which the $C_{14}$–$C_{20}$ alkyl groups are derived from hydrogenated tallow, sold under the name Rewoquat W75H® by Rewo Chemische, dialkylhydroxyethylmethyl-ammonium methyl sulphate in which the alkyl radicals are derived from hydrogenated or non-hydrogenated tallow, sold under the name Stepanquat VP 85® by Stepan, and Quaternium-82 sold by SEPPIC under the name Amonyl DM®.

The incorporation of these water-insoluble ionic amphiphilic lipids gives the cubic gel particles a surface charge which results in an electrostatic repulsion between each of the particles.

The oily phase in the compositions according to the invention preferably comprises at least one oil chosen from oils of plant or animal origin, mineral oils and synthetic oils. For example, the oils of plant origin may be, in particular, apricot kernel oil, sunflower oil, corn oil, soybean oil, marrow oil, grapeseed oil, blackcurrant seed oil, jojoba oil, sweet almond oil, safflower oil, sesame oil, borage oil, hazelnut oil, macadamia oil and the liquid fraction of karite butter. Plant oils that can also be used are essential oils such as eucalyptus oil, hybrid lavender oil, lavender oil, vetiver oil, Litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil. The oils of animal origin may be, for example, fish oils, turtle oil and mink oil as well as hydrogenated squalene (or perhydrosqualene). The mineral oils may be, for example, liquid paraffin and isoparaffms. The synthetic oils may be, for example, hydrocarbons, such as isohexadecane, polydecene and polyisobutene, fatty alcohols such as octyldodecanol, isostearyl alcohol and oleyl alcohol, esters such as glycerides of essential fatty acids, capric and caprylic acid triglycerides and mixtures thereof, esters of a fatty alcohol and of a linear or branched fatty acid, such as purcellin oil (cetearyl octanoate/isopropyl myristate) and the mixture of stearyl heptanoate and stearyl octanoate, sold under the name Dub Solid® by Stearineries Dubois. In addition, synthetic oils such as silicone oils of linear type, such as polydimethylsiloxane, of cyclic type, such as cyclopentadimethylsiloxane and cyclohexadimethylsiloxane, and of organomodified type, such as polyphenyltrimethylsiloxane and oxyethylenated and/or oxypropylenated polydimethylsiloxane may also be used in the invention. For example, synthetic fluoro oils such as perfluorodecahydronaphthalenes, for instance perfluorodecalin, as well as oils of perfluoro type, such as perfluoropolymethyl isopropyl ethers may be used.

A person skilled in the art will take care not to introduce into the composition of the invention, compounds of a nature or in an amount liable to prevent the preparation of a composition as defined according to the invention.

Needless to say, by virtue of the specific structure of the cubic gel particles, it is possible to incorporate therein both hydrophilic and lipophilic active principles, even though there is a certain level of incompatibility between these active principles. Various active principles can be incorporated into the composition, particularly antioxidants or anti-free-radical agents such as complexing agents and chelating agents (EDTA, tocopherol and esters thereof); hydrating agents or wetting agents such as polyols (glycerol, sorbitol), hyaluronic acid and the sodium salt thereof; UV screening agents; keratolytic agents such as retinoic acid and hydroxy acids such as salicylic acid and derivatives thereof; tanning accelerators such as caffeine and tyrosine derivatives; depigmenting agents such as kojic acid, vitamin C and its derivatives such as magnesium ascorbyl phosphate, arbutin and its derivatives; dyestuffs; self-tanning agents such as dihydroxyacetone and indoles; liporegulators such as γ-orizanol, extract of Centella asiatica, caffeine and theophylline; anti-ageing and anti-wrinkle agents such as hydroxy acids and in particular α-hydroxy acids, for instance glycolic acid, lactic acid and derivatives thereof, retinol and its derivatives, for instance retinol acetate, palmitate and propionate, and retinoids; anti-inflammatory agents and cicatrizing agents, such as 18-β-glycyrrhetinic acid and its salts, α-bisabolol; corticoids and extract of Centella asiatica, antibacterial and antifungal agents; insect repellents; deodorants; anti-dandruff agents; agents for preventing hair loss, such as methyl or hexyl nicotinate and Minoxidil; hair dyes such as oxidation bases and oxidation couplers, direct dyes and auto-oxidizable dyes; reducing agents for permanent-waving operations; skin and hair conditioners.

In the compositions of the invention. it is possible to use either cubic gel particles containing no active principles, or particles containing at least one hydrophilic or lipophilic active principle, or alternatively particles containing both at least one hydrophilic active principle and at least one lipophilic active principle. It is also possible to incorporate at least one active principle into the oily phase and/or into the aqueous phase. This active principle can be chosen in particular from the active principles as defined above.

The compositions according to the invention can also contain various conventional additives, for example, preserving agents, fragrances, pigments ($TiO_2$), dyestuffs, fillers and hydrophilic or lipophilic gelling agents.

Hydrophillic gelling agents which can be used may include, for example, cellulose derivatives such as hydroxyethylcellulose and alkylhydroxyethylcelluloses such as cetylhydroxy-ethylcellulose; alga derivatives such as satiagum; natural gums such as gum tragacanth or guar gum; synthetic polymers such as carboxyvinyl polymers or copolymers and in particular those sold under the names Carbopol® by Goodrich or Synthalen® by 3V SA. The proportion of gelling agent preferably ranges from 0.1 to 2% relative to the total weight of the composition.

The composition according to the invention is preferably made by a process comprising at least two steps. The first step generally consists of preparing an aqueous dispersion of cubic gel particles, as described above, by fragmentation using a homogenizer. The cubic gel is formed using at least two compounds as defined above, and water, optionally in the presence of water-insoluble ionic amphiphilic lipids and/or hydrophilic and/or lipophilic active principles and/or a dispersing and stabilizing agent as defined above. The homogenizer can be of the rotor-stator type with a high shear gradient, such as Virtis® or Heidolph Diax 600® or a high-pressure homogenizer operating at between 200 and 1800 bar approximately (20 to 180 Mpa). It is possible to introduce various additives and/or active principles into the aqueous phase, at this stage in the preparation of the aqueous dispersion of the cubic gel particles. After the formation of the cubic gel particles, the dispersing and stabilizing agent is generally outside of the cubic gel particles.

The second step then generally consists of adding an oily phase optionally containing certain additives and/or lipophilic active principles to the dispersion obtained, and subjecting the mixture to mechanical stirring which can be carried out, for example, using a homogenizer of the type described above.

At this stage of the process, various additives and/or active principles can also be introduced. When a gelled dispersion is desired, an aqueous solution containing a gelling agent is generally added to the mixture obtained after the second step.

The composition of the invention is intended especially for topical use and in particular cosmetic, dermatological and/or pharmaceutical use. For such applications, the composition may be incorporated into a physiologically acceptable medium, i.e. a medium which is compatible with the skin, tissues, mucous membranes and/or the hair of human beings is required. This composition can be fluid to a greater or lesser extent, can be white or colored, and can have the appearance of a cream, an ointment, a milk, a lotion, a serum, a paste or a mousse.

The composition of the invention can be applied topically, for example, particularly to the face, including the area around the eyes, to the body and to the scalp and keratin fibers such as the hair and the eyelashes of human beings.

The compositions of the invention find their application in a large number of cosmetic and/or dermatological treatments of the skin, mucous membranes, more especially the lips, and the hair, including the scalp.

The compositions according to the invention can be used, for example, on the skin (of the face or the body), mucous membranes, the scalp and/or keratin fibers such as the hair and the eyelashes, as care products and/or cleansing products and/or conditioners, as make-up products by incorporation of fillers, pigments or dyes, and as anti-sun products after introduction of suitable pigments, fillers and/or screening agents.

Another subject of the invention consists of a treatment process to care for and/or cleanse and/or condition and/or make-up and/or protect the skin, keratin fibers, the scalp and/or mucous membranes, which consists in applying a composition as defmed above to the skin, keratin fibers, the scalp and/or mucous membranes.

Another subject of the invention is the use of the composition according to the invention for the preparation of a therapeutic composition intended for the treatment and/or care of the skin, keratin fibers, the scalp and/or mucous membranes.

Other advantages and characteristics of the invention will emerge more clearly on reading the examples given by way of non-limiting illustration.

Obviously, numerous modifications and variations on the present invention are possible in light of the above teachings. It is therefore to be understood that within the scope of the appended claims, the invention may be practiced otherwise than as specifically described herein.

EXAMPLE 1

O/W Emulsion

| First phase: | |
|---|---|
| Diglyceryl isostearate | 1.2% |
| Diglyceryl di-/trioleate | 1.8% |
| Demineralized water | 54% |
| Glycerol | 3% |
| Polysorbate-40 (Montanox 40 DF ®) | 1% |
| Second phase: | |
| Apricot kernel oil | 6% |
| Perhydrosqualene | |
| Cyclopentadimethylsiloxane | 2% |
| Third phase: | |
| Cetylhydroxyethylcellulose (Natrosol Plus Grade 330 CS ® (the Aqualon company) | 1% |
| Preserving agents | 0.3% |
| Demineralized water | 23.7% |

EXAMPLE 2

W/O Emulsion

| First phase: | |
|---|---|
| Diglyceryl monooleate | 0.9% |
| Diglyceryl di-/trioleate | 1.65% |
| Demineralized water | 79.34% |
| Glycerol | 2.5% |
| Polysorbate-40 (Montanox 40 DF ®) | 0.21% |
| Preserving agents | 0.3% |
| Second phase: | |
| Stearyl heptanoate/stearyl octanoate | 3.5% |
| Jojoba oil | 4.2% |
| Cyclopentadimethylsiloxane | 6.2% |
| Cyclohexadimethylsiloxane | 1.2% |

EXAMPLE 3

W/O Emulsion

| First phase: | |
|---|---|
| Diglyceryl monooleate | 0.89% |
| Diglyceryl di-/trioleate | 1.65% |
| Monosodium stearoylglutamate | 0.01% |
| Demineralized water | 78.85% |
| Glycerol | 3% |
| Preserving agents | 0.3% |
| Second phase: | |
| Stearyl heptanoate/stearyl octanoate | 3.6% |
| Apricot kernel oil | 4.4% |
| Cyclopentadimethylsiloxane | 7.3% |

EXAMPLE 4

O/W Emulsion

| First phase: | |
|---|---|
| Diglyceryl isostearate | 1.8% |
| Diglyceryl 2-decyltetradecanoate | 1.2% |
| Monocetyl phosphate | 0.03% |
| Demineralized water | 54.95% |
| Glycerol | 3% |
| Triethanolamine | 0.01% |
| Second phase: | |
| Perhydrosqualene | 7% |
| Apricot kernel oil | 7% |
| Third phase: | |
| Carbomer (Carbopol 980 ® supplied by the company Goodrich) | 0.4% |
| Triethanolamine | 0.4% |
| Preserving agents | 0.3% |
| Demineralized water | 23.91% |

The priority document of the present application, French patent application 9808559, filed Jul. 3, 1998, is incorporated herein by reference.

We claim:

1. A composition comprising:
    an aqueous phase;
    an oily phase;
    at least one first amphiphilic compound capable of forming a lamellar phase in the presence of water; and
    at least one second amphiphilic compound capable of forming an inverse hexagonal phase in the presence of water;
    wherein said first amphiphilic compound and said second amphiphilic compound form cubic gel particles when mixed together in the presence of water,
    wherein said first amphiphilic compound is diglyceryl monooleate, and
    wherein said second amphiphilic compound is N-2-dodecylhexadecyloxycarbonyl-N-methyl-D-glucamine.

2. The composition of claim 1, comprising a mixture of said first amphiphilic compound and said second amphiphilic compound, wherein said first amphiphilic compound comprises 10–90 wt. % of said mixture and said second amphiphilic compound comprises 10–90 wt. % of said mixture.

3. The composition of claim 1, wherein said first amphiphilic compound and said second amphiphilic compound together constitute 0.1–15 wt. % of the total weight of the composition.

4. The composition of claim 1, wherein a weight ratio of said cubic gel particles to said oily phase is in the range of 0.02/1 to 1/1.

5. The composition of claim 1, wherein said oily phase is 2 to 40 wt. % of the total weight of said composition.

6. The composition of claim 1, wherein said cubic gel particles have a size ranging from 0.05 $\mu$m to 1 $\mu$m.

7. The composition of claim 1, wherein said composition is an oil-in-water emulsion, said oily phase comprising dispersed droplets, said droplets ranging in size from 0.1 to 10 $\mu$m.

8. The composition of claim 1, wherein said composition is a water-in-oil emulsion.

9. The composition of claim 1, further comprising a surfactant that is water-soluble at room temperature;
    wherein said surfactant contains at least one alkyl group, and each said alkyl group is linear or branched, saturated or unsaturated and each said alkyl group contains 8–22 carbon atoms.

10. The composition of claim 9, wherein said surfactant comprises at least one member selected from the group consisting of:
    (i) alkyl or alkenyl ethers or esters of a polyol;
    (ii) N-acyl amino acids and derivatives thereof, as well as peptides N-acylated with an alkyl or alkenyl radical, and the salts thereof;
    (iii) alkyl or alkenyl ether or ester sulphates, derivatives thereof and salts thereof;
    (iv) polyoxyethylenated fatty alkyl or alkenyl ethers or esters;
    (v) polyoxyethylenated alkyl- or alkenylcarboxylic acids and salts thereof;
    (vi) N-alkyl or alkenyl betaines;
    (vii) alkyl- or alkenyltrimethylammonium and salts thereof; wherein said alkyl and alkenyl groups contain 8–22 carbon atoms.

11. The composition of claim 1, further comprising at least one water-insoluble ionic amphiphilic lipid.

12. The composition of claim 1, wherein said oily phase comprises at least one oil selected from the group consisting of oils derived from plants or animals, mineral oils and synthetic oils.

13. The composition of claim 1, wherein said cubic gel particles contain at least one active principle, said active principle comprising at least one member selected from the group consisting of antioxidants, anti-free-radical agents, complexing agents, chelating agents, hydrating and wetting agents, UV screening agents, keratolytic agents, tanning accelerators, depigmenting agents, dyestuffs, self-tanning agents, liporegulators, anti-ageing and anti-wrinkle agents, anti-inflammatory agents and cicatrizing agents, corticoids, antibacterial and antifungal agents, insect repellents, deodorants, anti-dandruff agents, agents for preventing hair loss, hair dyes, reducing agents for permanent-waving operations, and skin and hair conditioners.

14. The composition of claim 1, further comprising at least one gelling agent.

15. The composition of claim 14, wherein said gelling agent comprises at least one member of the group consisting of cellulose derivatives, alga derivatives, natural gums and synthetic polymers.

16. A process for treating skin, keratin fibers, or mucous membranes, comprising:
    applying the composition of claim 1 to said skin, said keratin fibers, or said mucous membranes.

* * * * *

UNITED STATES PATENT AND TRADEMARK OFFICE
CERTIFICATE OF CORRECTION

PATENT NO.   : 6,506,391 B1
DATED        : January 14, 2003
INVENTOR(S)  : Bruno Biatry It is certified that error appears in the above-identified patent and that said Letters Patent is hereby corrected as shown below:

Column 10,
Line 34, "betaines;" should read -- betaines; and --;
Line 60, "alga" should read -- algal --.

Signed and Sealed this

Twenty-second Day of April, 2003

JAMES E. ROGAN
*Director of the United States Patent and Trademark Office*